United States Patent
Thornton, Jr.

(10) Patent No.: US 9,429,713 B2
(45) Date of Patent: Aug. 30, 2016

(54) SELF-CLEANING OPTICAL CONNECTOR

(71) Applicant: BOSTON SCIENTIFIC SCIMED, INC., Maple Grove, MN (US)

(72) Inventor: Peter Thornton, Jr., Los Altos, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/686,242

(22) Filed: Apr. 14, 2015

(65) Prior Publication Data

US 2015/0301288 A1 Oct. 22, 2015

Related U.S. Application Data

(60) Provisional application No. 61/981,075, filed on Apr. 17, 2014.

(51) Int. Cl.
  *G02B 6/38* (2006.01)
  *A61B 5/00* (2006.01)
  *A61B 5/0215* (2006.01)

(52) U.S. Cl.
  CPC .......... *G02B 6/3807* (2013.01); *A61B 5/0215* (2013.01); *A61B 5/02154* (2013.01); *A61B 2560/0285* (2013.01); *A61B 2562/228* (2013.01); *A61B 2562/245* (2013.01)

(58) Field of Classification Search
  None
  See application file for complete search history.

(56) References Cited

U.S. PATENT DOCUMENTS

| | | | |
|---|---|---|---|
| 3,963,323 A | 6/1976 | Arnold | |
| 4,771,782 A | 9/1988 | Millar | |
| 4,953,553 A | 9/1990 | Tremulis | |
| 5,106,455 A | 4/1992 | Jacobsen et al. | |
| 5,178,159 A | 1/1993 | Christian | |
| 5,238,004 A | 8/1993 | Sahatjian et al. | |
| 5,313,957 A | 5/1994 | Little | |
| 5,421,195 A | 6/1995 | Wlodarczyk | |
| 5,422,969 A | 6/1995 | Eno | |
| 5,427,114 A | 6/1995 | Colliver et al. | |
| 5,438,873 A | 8/1995 | Wlodarczyk et al. | |
| 5,573,520 A | 11/1996 | Schwartz et al. | |
| 5,633,963 A | 5/1997 | Rickenbach et al. | |
| 5,755,668 A | 5/1998 | Itoigawa et al. | |
| 5,772,609 A | 6/1998 | Nguyen et al. | |

(Continued)

FOREIGN PATENT DOCUMENTS

| DE | 202014100938 U1 | 3/2014 |
|---|---|---|
| EP | 0235992 A1 | 9/1987 |

(Continued)

*Primary Examiner* — Jerry Rahll
(74) *Attorney, Agent, or Firm* — Seager, Tufte & Wickhem, LLP

(57) ABSTRACT

An example medical device system includes a reusable connector cable having a female adaptor and a first fiber optic cable disposed within the reusable connector cable. A single use device is capable of connecting to the reusable connector cable and includes a male adaptor capable of mating with the female adaptor. A second fiber optic cable extends through the single use device such that the second fiber optic cable optically connects to the first fiber optic cable when the male adaptor of the single use device is disposed within the female adaptor of the reusable connector cable. A cleaning assembly is disposed within the single use device and is capable of cleaning an end of the first fiber optic cable when the male adaptor of the single use device is mated with the female adaptor of the reusable connector cable.

20 Claims, 8 Drawing Sheets

(56) References Cited

U.S. PATENT DOCUMENTS

| | | |
|---|---|---|
| 5,797,856 A | 8/1998 | Frisbie et al. |
| 5,872,879 A | 2/1999 | Hamm |
| 5,902,248 A | 5/1999 | Millar et al. |
| 5,938,624 A | 8/1999 | Akerfeldt et al. |
| 5,949,929 A | 9/1999 | Hamm |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,508,803 B1 | 1/2003 | Horikawa et al. |
| 6,565,514 B2 | 5/2003 | Svanerudh et al. |
| 6,579,246 B2 | 6/2003 | Jacobsen et al. |
| 6,585,660 B2 | 7/2003 | Dorando et al. |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huennekens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,461,997 B2 | 6/2013 | Samuelsson et al. |
| 8,485,985 B2 | 7/2013 | Manstrom et al. |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,936,401 B2 | 1/2015 | Belleville et al. |
| 8,998,823 B2 | 4/2015 | Manstrom et al. |
| 9,052,466 B2 | 6/2015 | Belleville et al. |
| 2003/0069522 A1 | 4/2003 | Jacobsen et al. |
| 2004/0073141 A1 | 4/2004 | Hartley et al. |
| 2004/0181174 A2 | 9/2004 | Davis et al. |
| 2005/0000294 A1 | 1/2005 | Tenerz et al. |
| 2005/0141817 A1 | 6/2005 | Yazaki et al. |
| 2006/0122537 A1 | 6/2006 | Reynolds et al. |
| 2008/0119758 A1 | 5/2008 | Samuelsson et al. |
| 2009/0082678 A1 | 3/2009 | Smith |
| 2009/0192412 A1 | 7/2009 | Sela et al. |
| 2010/0145308 A1 | 6/2010 | Layman et al. |
| 2010/0241008 A1 | 9/2010 | Belleville et al. |
| 2011/0071407 A1 | 3/2011 | Hübinette et al. |
| 2011/0178413 A1 | 7/2011 | Schmitt et al. |
| 2011/0186294 A1 | 8/2011 | Narvaez et al. |
| 2011/0229094 A1 | 9/2011 | Isenhour et al. |
| 2011/0319773 A1 | 12/2011 | Kanz et al. |
| 2012/0227505 A1 | 9/2012 | Belleville et al. |
| 2012/0265102 A1 | 10/2012 | Leo et al. |
| 2013/0051731 A1 | 2/2013 | Belleville et al. |
| 2013/0218032 A1 | 8/2013 | Belleville |
| 2013/0296718 A1 | 11/2013 | Ranganathan et al. |
| 2013/0317372 A1 | 11/2013 | Eberle et al. |
| 2014/0005558 A1 | 1/2014 | Gregorich |
| 2014/0058275 A1 | 2/2014 | Gregorich et al. |
| 2014/0081244 A1 | 3/2014 | Voeller et al. |
| 2014/0107624 A1 | 4/2014 | Belleville |
| 2014/0121475 A1 | 5/2014 | Alpert et al. |
| 2014/0241669 A1 | 8/2014 | Belleville et al. |
| 2014/0248021 A1 | 9/2014 | Belleville et al. |
| 2015/0323747 A1* | 11/2015 | Leigh .................. G02B 6/38 385/61 |

FOREIGN PATENT DOCUMENTS

| | | |
|---|---|---|
| EP | 0738495 A1 | 10/1996 |
| EP | 0879615 A1 | 11/1998 |
| EP | 0879617 A1 | 11/1998 |
| EP | 1479407 A1 | 11/2004 |
| EP | 1925958 A1 | 5/2008 |
| GB | 2300978 A | 11/1996 |
| JP | 53141644 A | 12/1978 |
| JP | 2008304731 A | 12/2008 |
| WO | 9313707 A1 | 7/1993 |
| WO | 9533983 A1 | 12/1995 |
| WO | 9945352 A1 | 9/1999 |
| WO | 2007058616 A1 | 5/2007 |
| WO | 2008034010 A2 | 3/2008 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012090210 A1 | 7/2012 |
| WO | 2013033489 A1 | 3/2013 |
| WO | 2014025255 A1 | 2/2014 |
| WO | 2015059311 A1 | 4/2015 |

\* cited by examiner

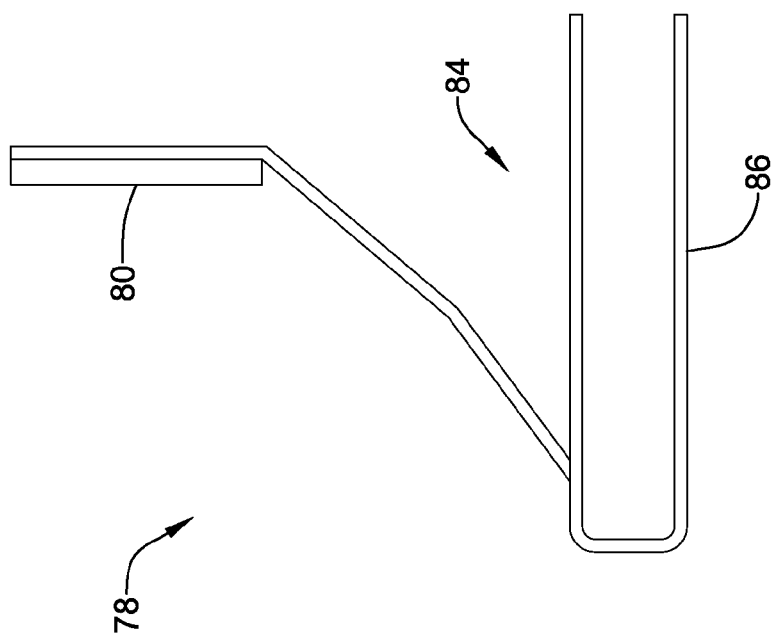

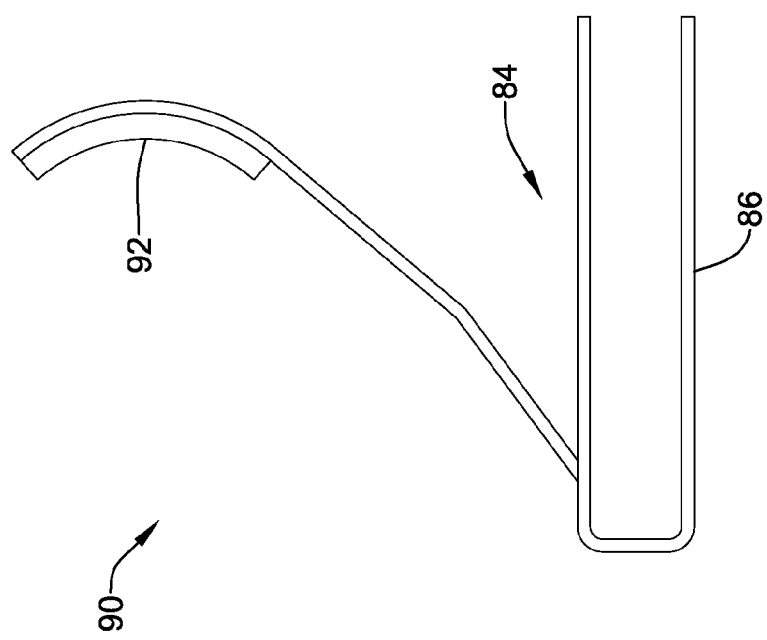

SELF-CLEANING OPTICAL CONNECTOR

CROSS-REFERENCE TO RELATED APPLICATIONS

This application claims priority under 35 U.S.C. §119 to U.S. Provisional Application Ser. No. 61/981,075, filed Apr. 17, 2014, the entirety of which is incorporated herein by reference.

TECHNICAL FIELD

The present disclosure pertains to medical devices, and methods for using and manufacturing medical devices. More particularly, the present disclosure pertains to medical devices and methods that include self-cleaning optical connectors.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example medical device system is disclosed. The medical device comprises:
 a reusable connector cable including a female adaptor;
 a first fiber optic cable disposed within the reusable connector cable;
 a single use device capable of connecting to the reusable connector cable, the single use device including a male adaptor capable of mating with the female adaptor of the reusable connector cable;
 a second fiber optic cable extending through the single use device such that the second fiber optic cable optically connects to the first fiber optic cable when the male adaptor of the single use device is disposed within the female adaptor of the reusable connector cable; and
 a cleaning assembly disposed within the single use device, capable of cleaning an end of the first fiber optic cable when the male adaptor of the single use device is mated with the female adaptor of the reusable connector cable.

Alternatively or additionally to any of the embodiments above, the single use device comprises a single use connector cable including the male adaptor at a first end and capable of connecting at a second end to a pressure sensing guidewire.

Alternatively or additionally to any of the embodiments above, the single use device comprises a pressure sensing guidewire including the male adaptor at a first end thereof.

Alternatively or additionally to any of the embodiments above, the reusable connector cable is operably connected to a signal processing module.

Alternatively or additionally to any of the embodiments above, the cleaning assembly is secured to the male adaptor of the single use device.

Alternatively or additionally to any of the embodiments above, the cleaning assembly comprises a wiping surface that is capable of wiping the end of the first fiber optic cable.

Alternatively or additionally to any of the embodiments above, the cleaning assembly is biased to hold the wiping surface against the end of the first fiber optic cable Alternatively or additionally to any of the embodiments above, the second fiber optic cable is recessed within the male adaptor of the single use device.

Alternatively or additionally to any of the embodiments above, the male adaptor includes a pocket to accommodate the cleaning assembly when the cleaning assembly is moved into a collapsed configuration when the male adaptor of the single use device mates with the female adaptor of the reusable connector cable.

Alternatively or additionally to any of the embodiments above, the female adaptor of the reusable connector cable includes a vent that is positioned to correspond to the pocket when the male adaptor of the single use device mates with the female adaptor of the reusable connector cable.

A medical device system is disclosed. The medical device system comprises:
 a signal processing module;
 a reusable connector cable operably connectable to the signal processing module, the connector cable including a female adaptor;
 a first fiber optic cable disposed within the reusable connector cable;
 a single use connector cable including a male adaptor capable of mating with the female adaptor of the reusable connector cable;
 a second fiber optic cable extending through the single use connector cable such that the second fiber optic cable optically connects to the first fiber optic cable when the male adaptor of the single use connector cable is mated with the female adaptor of the reusable connector cable; and
 a cleaning assembly disposed within the single use device, capable of cleaning an end of the first fiber optic cable when the male adaptor of the single use connector is mated with the female adaptor of the reusable connector cable.

Alternatively or additionally to any of the embodiments above, the single use connector cable includes the male adaptor at a first end and is capable of connecting at a second end to a pressure sensing guidewire.

Alternatively or additionally to any of the embodiments above, the cleaning assembly is secured to the male adaptor of the single use device.

Alternatively or additionally to any of the embodiments above, the cleaning assembly comprises a wiping surface that is capable of wiping the end of the first fiber optic cable and the cleaning assembly is biased to hold the wiping surface against the end of the first fiber optic cable Alternatively or additionally to any of the embodiments above, the male adaptor of the single use connector cable protects an end of the second fiber optic cable.

Alternatively or additionally to any of the embodiments above, the male adaptor includes a pocket to accommodate the cleaning assembly when the cleaning assembly is moved into a collapsed configuration when the male adaptor of the single use device mates with the female adaptor of the reusable connector cable.

Alternatively or additionally to any of the embodiments above, the female adaptor of the reusable connector cable includes a vent that is positioned to correspond to the pocket when the male adaptor of the single use device mates with the female adaptor of the reusable connector cable.

A method of connecting a pressure sensing guidewire to a signal processing module is disclosed. The method comprises:

providing a connector cable operably connectable to the signal processing module, the connector cable including a female adaptor and a first fiber optic cable extending within the female adaptor;

providing a disposable cable including a male adaptor and a second fiber optic cable extending within the male adaptor;

providing a cleaning assembly disposed within the male adaptor;

advancing the male adaptor of the disposable cable into the female adaptor of the connector cable such that an end of the second fiber optic cable contacts the cleaning assembly; and further advancing the male adaptor of the disposable cable within the female adaptor of the connector cable such that the cleaning assembly cleans the end of the second fiber optic cable and is bent out of the way so that the first fiber optic cable can optically connect with the second fiber optic cable.

Alternatively or additionally to any of the embodiments above, the method further comprises connecting a pressure sensing guidewire to the disposable cable.

Alternatively or additionally to any of the embodiments above, the method further comprises obtaining a pressure measurement using the pressure sensing guidewire.

The above summary of some embodiments is not intended to describe each disclosed embodiment or every implementation of the present invention. The Figures, and Detailed Description, which follow, more particularly exemplify these embodiments.

BRIEF DESCRIPTION OF THE FIGURES

The present disclosure may be more completely understood in consideration of the following detailed description of various embodiments of the present disclosure in connection with the accompanying drawings, in which:

FIG. 7 is a schematic illustration of a cleaning assembly useful in the cable connector of FIG. 2; and FIG. 8 is a schematic illustration of another cleaning assembly useful in the cable connector of FIG. 2.

Figure 1:
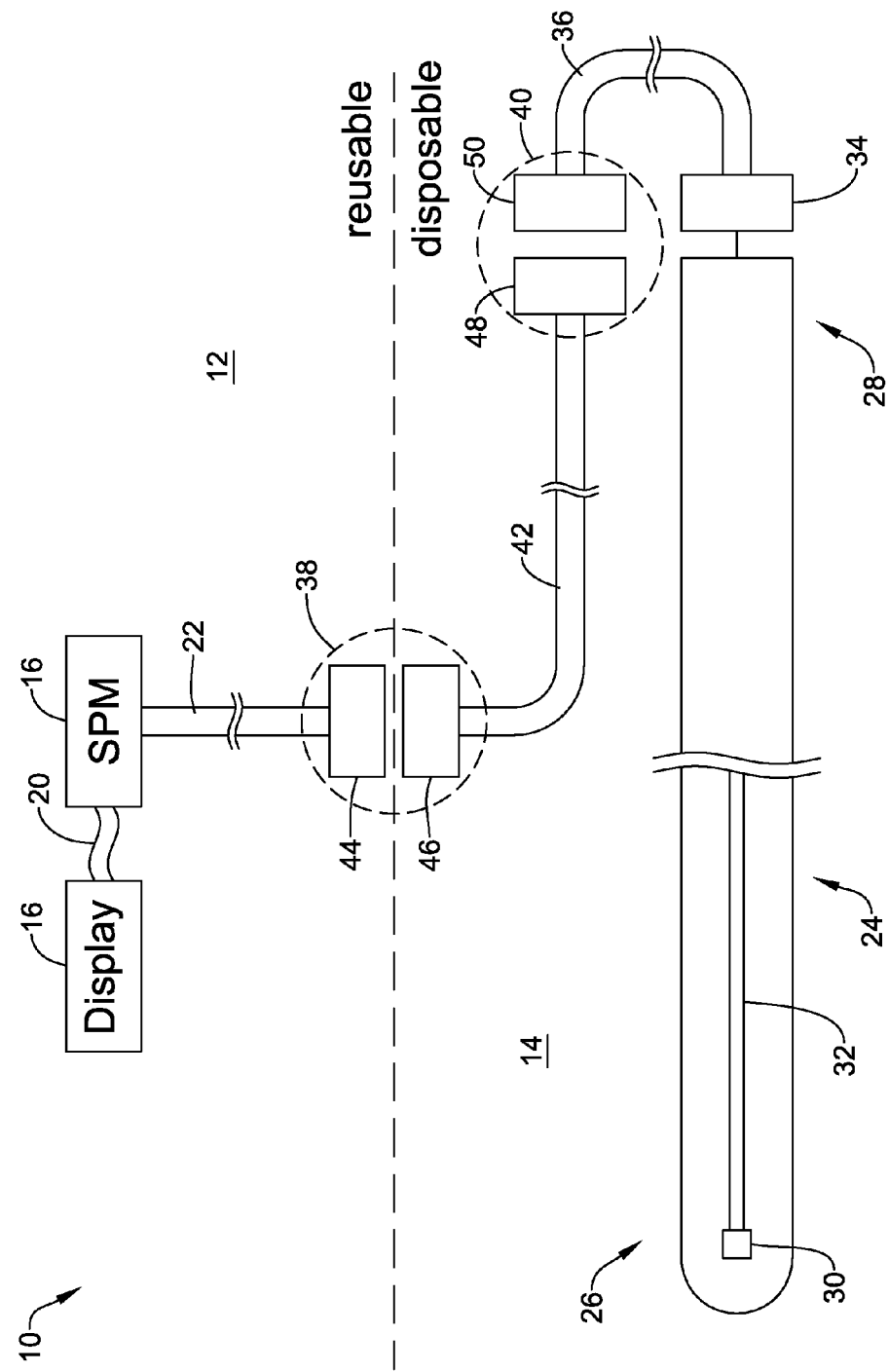
FIG. 1 is a schematic illustration of a medical device system including a pressure sensing guidewire.

While the present disclosure is amenable to various modifications and alternative forms, specifics thereof have been shown by way of example in the drawings and will be described in detail. It should be understood, however, that the intention is not to limit the present disclosure to particular embodiments described. On the contrary, the intention is to cover all modifications, equivalents, and alternatives falling within the spirit and scope of the present disclosure.

DETAILED DESCRIPTION

Definitions of certain term are provided below, and these definitions shall be applied, unless a different definition is given in the claims or elsewhere in this specification.

All numeric values used herein are assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents, unless the content clearly dictates otherwise. As used in this specification and the appended claims, the term "or" is generally employed in its sense including "and/or", unless the content clearly dictates otherwise.

The following detailed description should be read with reference to the drawings in which similar elements in different drawings are identified with the same reference numbers. The drawings, which are not necessarily to scale, depict illustrative embodiments and are not intended to limit the scope of the invention.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with one embodiment, it should be understood that such feature, structure, or characteristic may also be used in connection with other embodiments, whether or not explicitly described, unless cleared stated to the contrary.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis. A number of pressure sensing devices, however, may pose technical challenges for steering, tracking, torqueing or otherwise navigating the device within the vasculature. For example, medical devices may include a relatively stiff pressure sensor located at or near the distal tip of the device and/or a sensor housing (in which the sensor is mounted) that may also be relatively stiff. Disclosed herein are a number of medical device that include pressure sensing capabilities and may be more easily steered, tracked, torqued, and/or otherwise navigated through the anatomy.

FIG. 1 is a schematic view of an example system 10 for obtaining pressure measurements within a patient's anatomy. In some embodiments, the system 10 may be considered as including a reusable portion 12 and a disposable or one-time use portion 14. It will be appreciated that in some instances, one or more elements of the reusable portion 12 may instead be disposable or replaceable, and in some instances, one or more elements of the disposable portion 14 may be used more than once.

The reusable portion 12 includes some of the supporting devices that enable use of the disposable portion 14. In some embodiments, the reusable portion 12 includes a signal processing module 16. The signal processing module 16 may, for example, include a light source and may be configured to process optical signals that are received by the signal processing module 16. In some embodiments, as illustrated, the signal processing module 16 may communicate with a display 18 via a cable 20. The display 18 may represent data textually, graphically, or pictorially for diagnosing a medical condition within the body lumen. A clinician may utilize the readings from the display 18 to tailor the intervention to the needs of the patient or otherwise advance the goals of the intervention. The signal processing module 16 may be operably connectable to an optical cable 22 that enables communication between the signal processing module 16 and the disposable portion 14.

In some embodiments, the disposable portion 14 includes a pressure sensing guidewire 24 extending from a distal region 26 to a proximal region 28. At the distal region 26, the pressure sensing guidewire 24 may include a pressure sensor 30 that may be configured to obtain pressure measurements within the environment immediately outside of pressure sensing guidewire 24. Accordingly, the distal region 26 may include one or more apertures (not illustrated) to provide fluid communication between the environment and the pressure sensor 30.

While the pressure sensor 30 is shown schematically in FIG. 1, it can be appreciated that the structural form and/or type of the pressure sensor 30 may vary. For example, the pressure sensor 30 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

A fiber optic cable 32 is operably connected to the pressure sensor 30 and extends proximally therefrom. In some embodiments, the fiber optic cable 32 is a polymer fiber optic cable. In some embodiments, at least part or all of the fiber optic cable 32 may instead be a glass fiber optic cable. The fiber optic cable 32 permits optical signals to be communicated to and from the pressure sensor 30.

The system 10 includes one or more optical cables that are external to the pressure sensing guidewire 24 in order to carry optical signals between the pressure sensing guidewire 24 and the signal processing module 16. At the proximal region 28, the pressure sensing guidewire 24 may be configured to be attached to a connector or handle member 34. The handle 34 may include a suitable connector for an optical cable 36 to be attached to the handle 34. These are just examples. It will be appreciated that other devices and/or arrangements may be utilized with the pressure sensing guidewire 24.

In some embodiments, for example, a clinician may use the pressure sensing guidewire 24 to measure or calculate FFR (e.g., the pressure after an intravascular lesion relative to the pressure before the lesion). This may include taking an initial pressure reading before or upstream of the lesion and then a comparative reading after or downstream of the lesion. This may also include monitoring the pressure while advancing the pressure sensing guidewire 24 through a blood vessel until a pressure differential or drop in pressure is observed, indicating that the pressure sensing guidewire 24 has reached and/or partially past the lesion as well as monitoring increases in pressure during and/or following a treatment intervention. In some embodiments, a second pressure measuring device may be used to measure pressure at another intravascular location and this pressure may be utilized in the calculation of FFR or otherwise used as part of the intervention.

As illustrated, the system 10 may be considered as including a connector assembly 38 and a connector assembly 40. The connector assembly 38 may be considered as providing an optical connection between the optical cable 22 and an optical cable 42. Similarly, the connector assembly 40 may be considered as providing an optical connection between the optical cable 42 and the optical cable 36. In some embodiments, it is contemplated that the optical cable 42 may be optional, and thus the connector assembly 38 may provide an optical connection directly between the optical cable 22 and the optical cable 36. The optical cable 42, if present, may be considered as being a connector cable.

While the connector assembly 38 and the connector assembly 40 are described and illustrated herein as pertaining to medical devices, it will be appreciated that the features and elements of the connector assembly 38 and the connector assembly 40 may have application in other, non-medical, fields of endeavor.

As will be discussed, the connector assembly 38 may be considered as including a female adaptor 44 at an end of the optical cable 22 and a corresponding male adaptor 46 at an end of the optical cable 42. The male adaptor 46 may be configured to fit within the female adaptor 44. In this, it will be appreciated that the terms male and female are used for convenience and generally an element labeled as male fits within an element labeled as female. These elements could just as easily be referred to as a first element and a second element. The connector assembly 40, if present, may be considered as including a female adaptor 48 at an end of the optical cable 42 and a corresponding male adaptor 50 at an end of the optical cable 36. The male adaptor 50 may be configured to fit within the female adaptor 48. If the optical cable 42 is absent, the connector assembly 38 would include the female adaptor 44 and the male adaptor 50.

Figure 2:
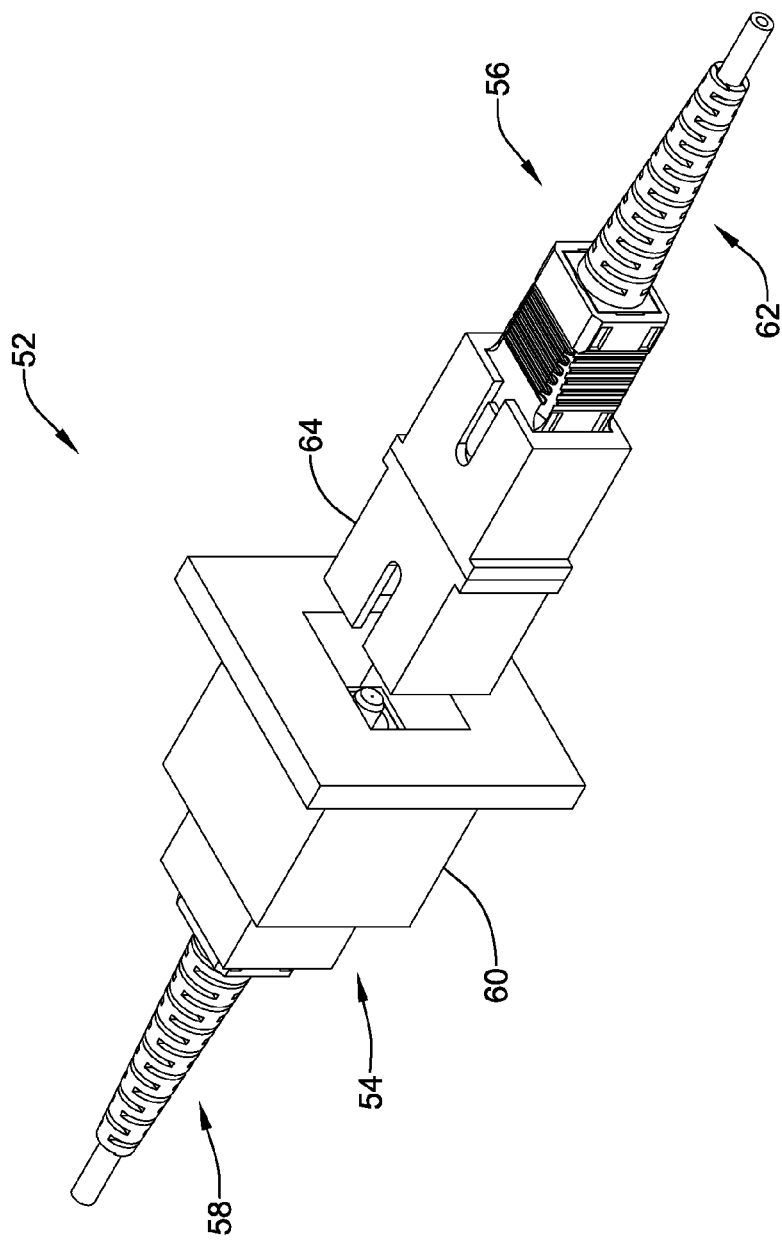
FIG. 2 is a perspective view of a cable connector useful in the medical device system of FIG. 1.
Figure 4:
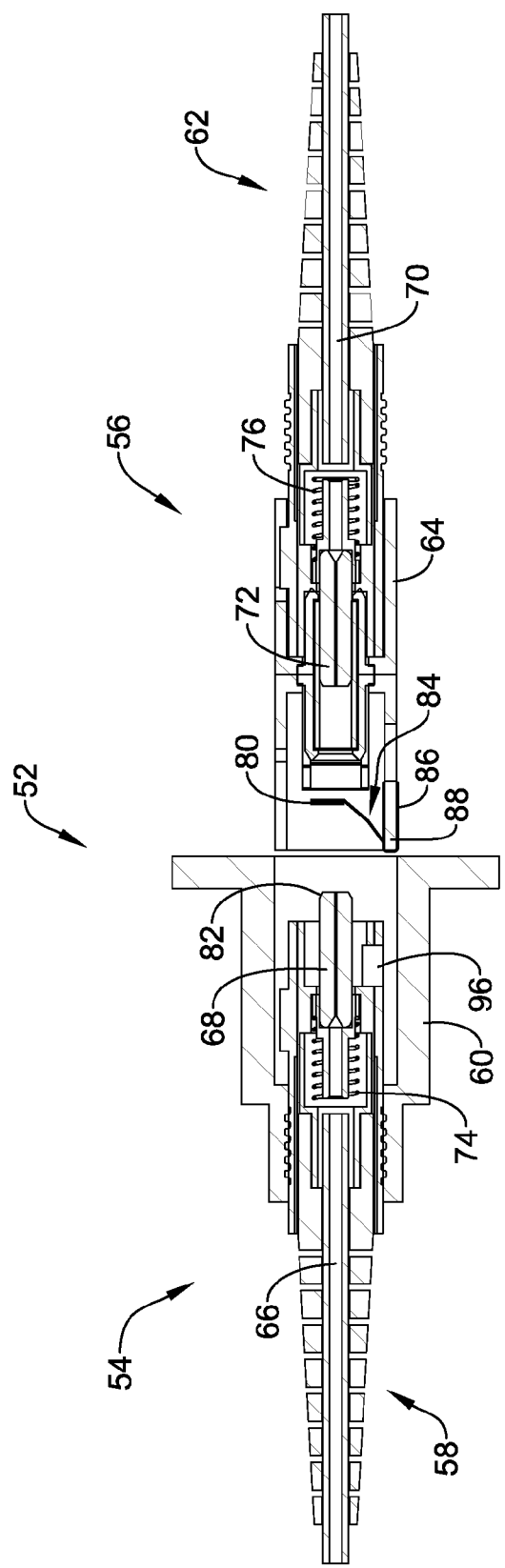
FIG. 4 is a cross-sectional view of the cable connector of FIG. 2.

FIG. 2 is a perspective view and FIG. 4 is a cross-sectional view of a connector assembly 52 that may be considered as representing either the connector assembly 38 or the connector assembly 40. The connector assembly 52 may be considered as including a first portion 54 and a second portion 56. The first portion 54 includes a cable 58 and a female adaptor 60 at an end thereof. The second portion 56 includes a cable 62 and a male adaptor 64 at an end thereof. It will be appreciated that in some embodiments, and with reference to the system 10 described in FIG. 1, the first portion 54 may represent a reusable portion while the second portion 56 may represent a disposable portion, but this is not required.

Figure 3:
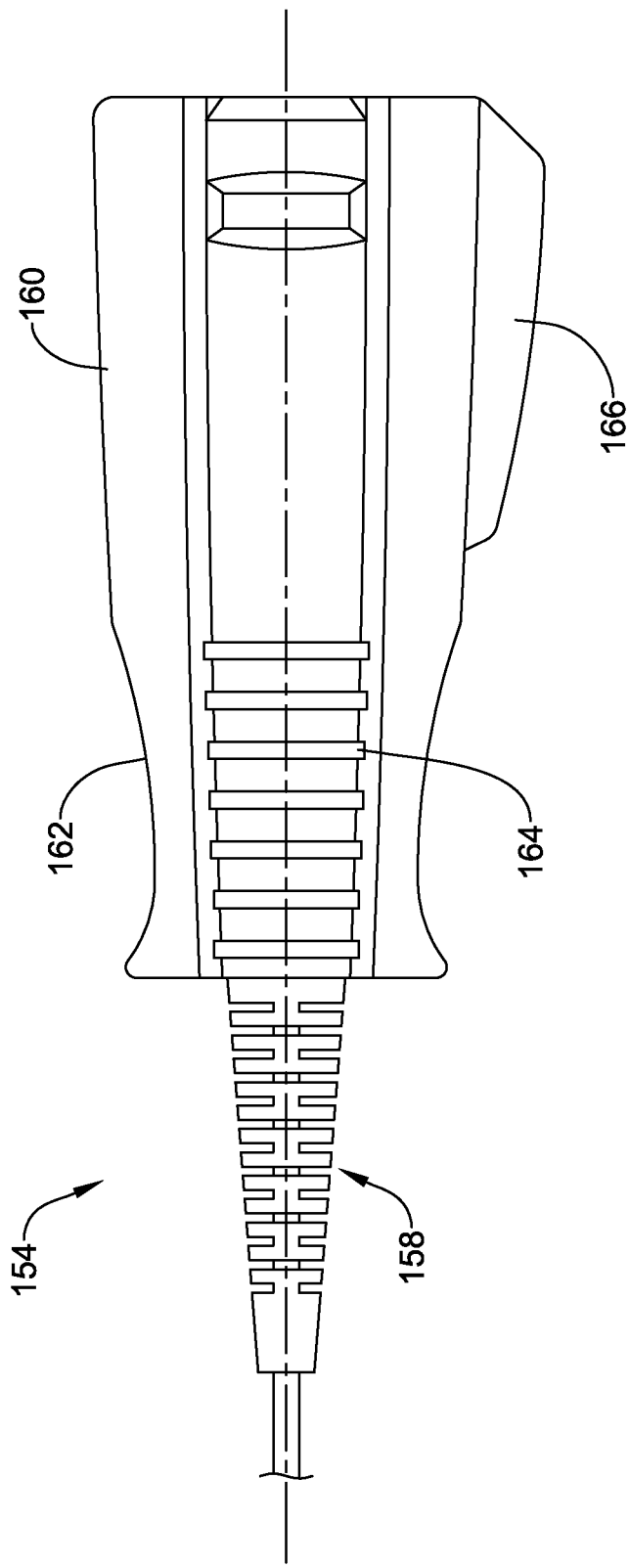
FIG. 3 is a top plan view of a portion of a cable connector useful in the medical device system of FIG. 1.

It will be appreciated that the female adaptor 60 shown in FIGS. 2 and 4 is illustrative only, as this element may take other shapes as well. Turning briefly to FIG. 3, another embodiment of the first portion 54 is illustrated. In FIG. 3, a first portion 154 includes a female adaptor or sheath 160 and a cable 158 extending from the female adaptor 160. In some embodiments, as illustrated, the female adaptor 160 may include features that enable a user to better grip the first portion 154. For example, the female adaptor 160 may include one or more features such as a reduced diameter portion 162 that may be sized to accommodate a user's thumb and/or knurling 164 that may help to provide a better grip. A fin 166, if present, may be of assistance in orienting the first portion 154.

Returning to FIG. 4, the first portion 54 includes a fiber optic cable 66 having a contact portion 68 while the second portion 56 includes a fiber optic cable 70 having a contact portion 72. It will be appreciated that in some embodiments, the contact portion 68 is at least partially protected by the female adaptor 60 and the contact portion 72 is at least partially protected by the male adaptor 64 while the first portion 54 and the second portion 56 are separated from each other, before they are connected.

In some embodiments, as illustrated, the contact portion 68 is biased via a spring 74 and the contact portion 72 is biased via a spring 76. The springs 74, 76, if present, help to hold the contact portion 68 against the contact portion 72 when the first portion 54 is fully inserted into the second portion 56, as will be demonstrated with respect to FIGS. 5 and 6. By helping to ensure good contact between the contact portion 68 and the contact portion 72, good optical transmission can occur through the connector assembly 52.

The connector assembly 52 includes a cleaning assembly 78. As best illustrated in FIG. 7, the cleaning assembly 78 includes a wiping surface 80 that is configured to contact and wipe a front surface 82 of the contact portion 68 and a support structure 84 that is configured to support the wiping surface 80 and to secure the cleaning assembly 78 to the male adaptor 64. In some embodiments, the support structure 84 may be formed of a resilient material such as stainless steel or spring steel in order to provide a biasing force to the wiping surface 80.

In the illustrated embodiment, the support structure 84 includes a U-shaped portion 86 that frictionally engages a wall portion 88 of the male adaptor 64. It will be appreciated that in some embodiments, the cleaning assembly 78 may instead be adhesively secured to the male adaptor 64. The wiping surface 80 may be formed from or otherwise includes an absorbent pad that includes a cleaning solution such as alcohol or any other suitable cleaner.

While the wiping surface 80 is illustrated as being largely planar in shape, it will be appreciated that in some embodiments, the wiping surface 80 may instead be non-planar. FIG. 8 illustrates a cleaning assembly 90 having a curved wiping surface 92. The curved wiping surface 92 may be either concave or convex in nature, in order to improve the cleaning action when the wiping surface 92 (or 80, in FIG. 7) moves across the front surface 82 of the contact portion 68.

Figure 5:
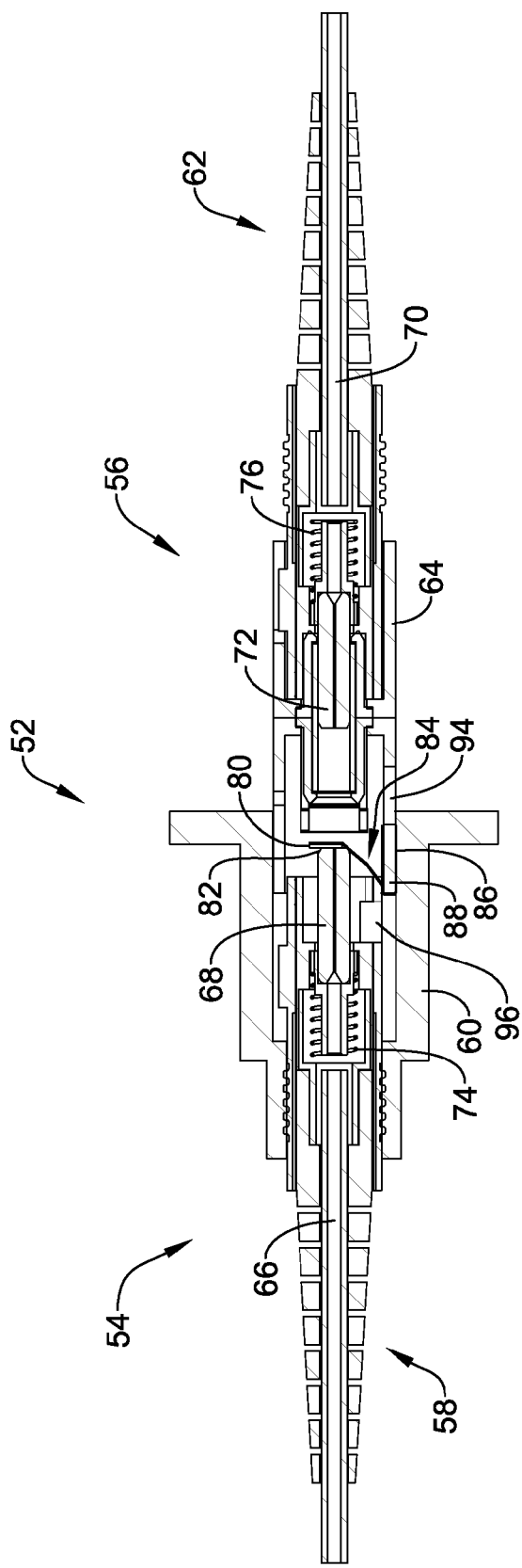
FIG. 5 is a cross-sectional view of the cable connector of FIG. 2, with a first part of the connector partially inserted into a second part of the connector.
Figure 6:
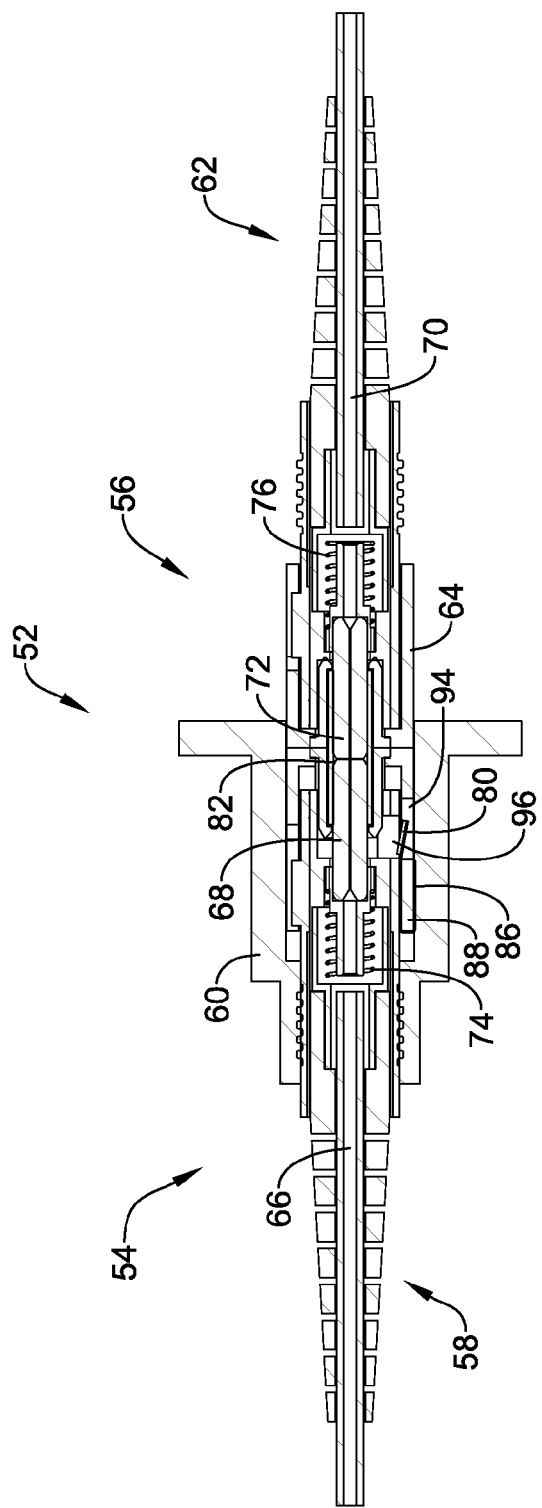
FIG. 6 is a cross-sectional view of the cable connector of FIG. 2, with the first part of the connector fully inserted into the second part of the connector.

FIGS. 5 and 6 provide an illustration of how the cleaning assembly 78 (or 88) cleans the front surface 82 of the contact portion 68. In FIG. 5, the male adaptor 64 has been partially inserted into the female adaptor 60 such that the wiping surface 80 (or 92) has just contacted the front surface 82 of the contact portion 68. In FIG. 6, the male adaptor 64 has been fully inserted into the female adaptor 60 such that the contact portion 68 and the contact portion 72 are in contact with each other such that optical communication through the connector assembly 52 can occur. It can be seen that the springs 72 and 74 have been partially compressed, and thus provide a biasing force to hold the contact portion 68 and the contact portion 72 in good contact with each other.

It can be seen, in comparing FIG. 6 to FIG. 5, that the cleaning assembly 78 (or 88) has been pushed out of the way. In some embodiments, the male adaptor 64 includes a pocket 94 that is positioned and sized to accommodate the cleaning assembly 78 (or 88) as the cleaning assembly 78 (or 88) is pushed out of the way. In some embodiments, the female adaptor 60 includes a corresponding vent 96, but this is not required.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as described in the following claims.

What is claimed is:

1. A medical device system comprising:
   a reusable connector cable including a female adaptor;
   a first fiber optic cable disposed within the reusable connector cable;
   a single use device capable of connecting to the reusable connector cable, the single use device including a male adaptor capable of mating with the female adaptor of the reusable connector cable;
   a second fiber optic cable extending through the single use device such that the second fiber optic cable optically connects to the first fiber optic cable when the male adaptor of the single use device is disposed within the female adaptor of the reusable connector cable; and
   a cleaning assembly disposed within the single use device, capable of cleaning an end of the first fiber optic cable when the male adaptor of the single use device is mated with the female adaptor of the reusable connector cable.

2. The medical device system of claim 1, wherein the single use device comprises a single use connector cable including the male adaptor at a first end and capable of connecting at a second end to a pressure sensing guidewire.

3. The medical device system of claim 1, wherein the single use device comprises a pressure sensing guidewire including the male adaptor at a first end thereof.

4. The medical device system of claim 1, wherein the reusable connector cable is operably connected to a signal processing module.

5. The medical device system of claim 1, wherein the cleaning assembly is secured to the male adaptor of the single use device.

6. The medical device system of claim 5, wherein the cleaning assembly comprises a wiping surface that is capable of wiping the end of the first fiber optic cable.

7. The medical device system of claim 6, wherein the cleaning assembly is biased to hold the wiping surface against the end of the first fiber optic cable.

8. The medical device system of claim 1, wherein the second fiber optic cable is recessed within the male adaptor of the single use device.

9. The medical device system of claim 1, wherein the male adaptor includes a pocket to accommodate the cleaning assembly when the cleaning assembly is moved into a collapsed configuration when the male adaptor of the single use device mates with the female adaptor of the reusable connector cable.

10. The medical device system of claim 9, wherein the female adaptor of the reusable connector cable includes a vent that is positioned to correspond to the pocket when the male adaptor of the single use device mates with the female adaptor of the reusable connector cable.

11. A medical device system comprising:
    a signal processing module;

a reusable connector cable operably connectable to the signal processing module, the connector cable including a female adaptor;

a first fiber optic cable disposed within the reusable connector cable;

a single use connector cable including a male adaptor capable of mating with the female adaptor of the reusable connector cable;

a second fiber optic cable extending through the single use connector cable such that the second fiber optic cable optically connects to the first fiber optic cable when the male adaptor of the single use connector cable is mated with the female adaptor of the reusable connector cable; and a cleaning assembly disposed within the single use device, capable of cleaning an end of the first fiber optic cable when the male adaptor of the single use connector is mated with the female adaptor of the reusable connector cable.

12. The medical device system of claim 11, wherein the single use connector cable includes the male adaptor at a first end and is capable of connecting at a second end to a pressure sensing guidewire.

13. The medical device system of claim 11, wherein the cleaning assembly is secured to the male adaptor of the single use device.

14. The medical device system of claim 13, wherein the cleaning assembly comprises a wiping surface that is capable of wiping the end of the first fiber optic cable and the cleaning assembly is biased to hold the wiping surface against the end of the first fiber optic cable.

15. The medical device system of claim 11, wherein the male adaptor of the single use connector cable protects an end of the second fiber optic cable.

16. The medical device system of claim 11, wherein the male adaptor includes a pocket to accommodate the cleaning assembly when the cleaning assembly is moved into a collapsed configuration when the male adaptor of the single use device mates with the female adaptor of the reusable connector cable.

17. The medical device system of claim 16, wherein the female adaptor of the reusable connector cable includes a vent that is positioned to correspond to the pocket when the male adaptor of the single use device mates with the female adaptor of the reusable connector cable.

18. A method of connecting a pressure sensing guidewire to a signal processing module, the method comprising:

providing a connector cable operably connectable to the signal processing module, the connector cable including a female adaptor and a first fiber optic cable extending within the female adaptor;

providing a disposable cable including a male adaptor and a second fiber optic cable extending within the male adaptor;

providing a cleaning assembly disposed within the male adaptor;

advancing the male adaptor of the disposable cable into the female adaptor of the connector cable such that an end of the second fiber optic cable contacts the cleaning assembly; and further advancing the male adaptor of the disposable cable within the female adaptor of the connector cable such that the cleaning assembly cleans the end of the second fiber optic cable and is bent out of the way so that the first fiber optic cable can optically connect with the second fiber optic cable.

19. The method of claim 18, further comprising connecting a pressure sensing guidewire to the disposable cable.

20. The method of claim 19, further comprising obtaining a pressure measurement using the pressure sensing guidewire.

* * * * *